United States Patent
Carlson et al.

[11] Patent Number: 6,030,356
[45] Date of Patent: *Feb. 29, 2000

[54] IRRIGATION CLIP

[75] Inventors: Glenn T. Carlson, Keller; Gary B. Gage, Arlington, both of Tex.

[73] Assignee: Midas Rex, L.P., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/040,741

[22] Filed: Mar. 18, 1998

[51] Int. Cl.⁷ ..................................................... A61B 17/20
[52] U.S. Cl. ............................................... 604/22; 604/46
[58] Field of Search .................................. 604/19, 22, 27, 604/35, 264, 280–533, 47, 46

[56] References Cited

U.S. PATENT DOCUMENTS 4,136,700  1/1979  Broadwin et al. .
4,562,838  1/1986  Walker .
5,624,393  4/1997  Diamond .

*Primary Examiner*—Wynn Wood Coggins
*Assistant Examiner*—Jennifer R. Sadula

[57] ABSTRACT

A disposable irrigation device for a motorized surgical tool comprises a cannula with a cylindrical clip bonded near one end. The clip has a C-shaped cross-section with a slot. Both the cannula and the clip are formed from malleable material which may be manually formed into a resilient desired shape. The surgical tool has a rotatable tool implement extending from a cylindrical guide member. The device is attached to the tool by inserting the guide member into the clip so that one end of the cannula is located near the implement. The malleable clip clamps around and frictionally engages the guide member. The malleable cannula may be bent to precisely direct the flow of irrigation fluid relative to the implement. For implements of greater length, the device may be inverted and attached in the opposite direction.

19 Claims, 1 Drawing Sheet

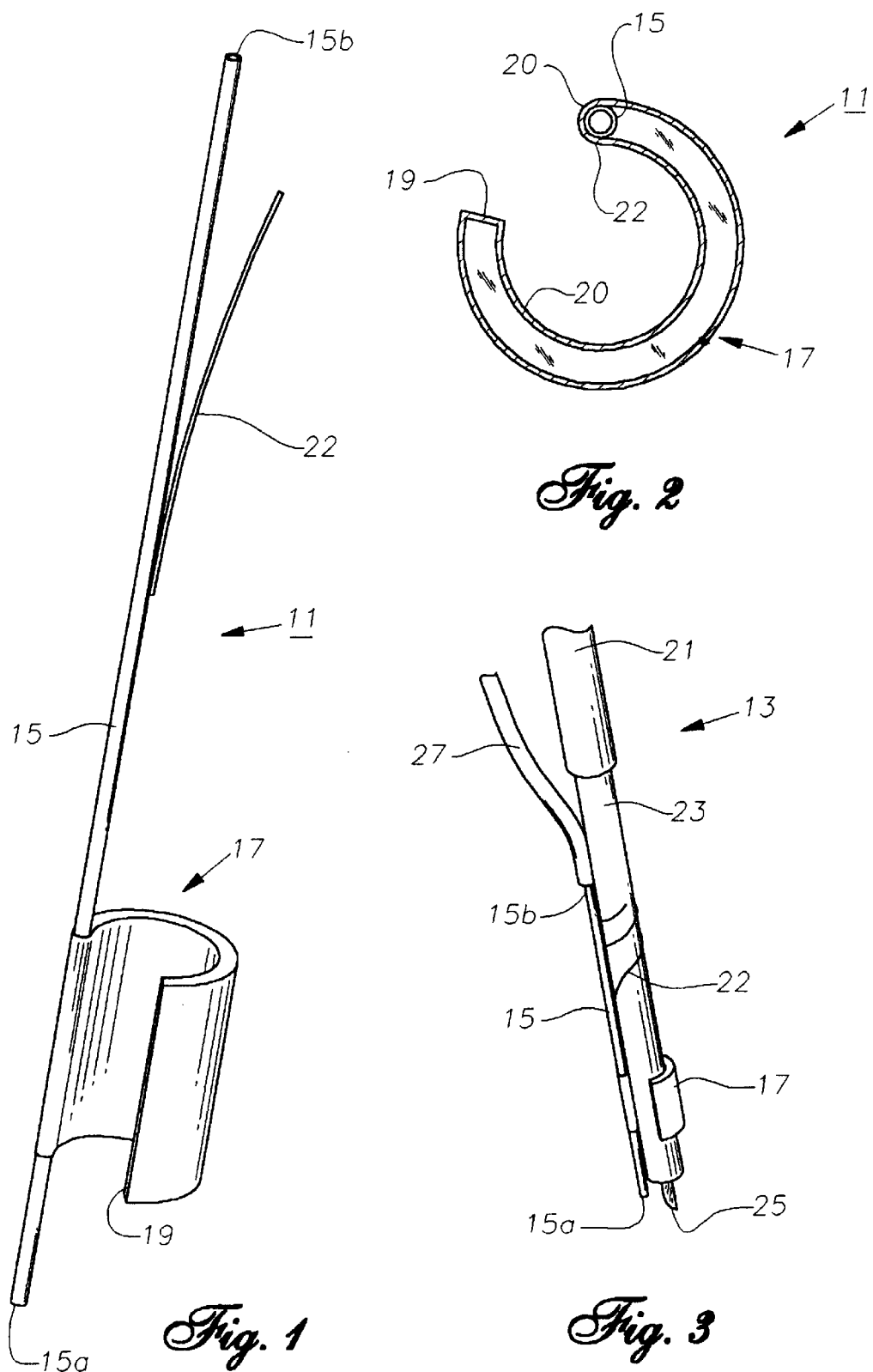

IRRIGATION CLIP

TECHNICAL FIELD

This invention relates in general to motorized surgical tools with and in particular to an improved irrigation device for motorized surgical tools.

BACKGROUND ART

Motorized surgical tools which are used to cut or resect human bone, such as in orthopedic surgery, utilize a pneumatic motor to rotate a cutting tool implement at high speeds. It is often necessary to irrigate the work site with a saline solution for cooling while the cutting is occurring.

One prior art device uses an irrigation tube which is secured to the surgical tool with C-shaped clips. The irrigation tube has a rigid nozzle on one end which directs fluid onto the tool implement. Another prior art device comprises a surgical tool with an integral conduit which directs a stream of fluid to the tool implement. A third prior art device comprises a rigid tube with a fixed outlet which is permanently mounted to the surgical tool. A more adaptable irrigation device is needed.

DISCLOSURE OF THE INVENTION

A disposable irrigation device for a motorized surgical tool comprises a tube with a cylindrical clip bonded near one end. The clip has a C-shaped cross-section with a slot. Both the tube and the clip are formed from malleable material which may be manually formed into a resilient desired shape. The surgical tool has a rotatable tool implement extending from a cylindrical guide member. The device is attached to the tool by inserting the guide member into the clip so that one end of the tube is located near the implement. The malleable clip clamps around and frictionally engages the guide member. The malleable tube may be bent to precisely direct the flow of irrigation fluid relative to the implement. For implements of greater length, the device may be inverted and attached in the opposite direction.

BRIEF DESCRIPTION OF THE DRAWINGS

FIG. 1 is an isometric view of an irrigation device constructed in accordance with the invention.

FIG. 2 is an end view of the irrigation device of FIG. 1.

FIG. 3 is a schematic view of the irrigation device of FIG. 1 mounted to a surgical tool.

BEST MODE FOR CARRYING OUT THE INVENTION

Referring to FIGS. 1 and 2, an irrigation device 11 for attachment to a motorized orthopedic surgical tool 13 (FIG. 3) is shown. Device 11 comprises a long cannula or tube 15 and a short cylindrical clip 17 rigidly mounted to one end. Tube 15 has two ends. End 15a is located closer to clip 17 while end 15b is located farther away from clip 17. Clip 17 is a C-shaped band which has a C-shaped cross-section (FIG. 2) and has a larger diameter than tube 15. Tube 15 has an outer diameter which is approximately equal to a radial thickness of clip 17. In the preferred embodiment, tube 15 is permanently affixed or bonded to clip 17 such that their longitudinal axes are parallel to one another. Clip 17 has a narrow longitudinal slot 19 with two parallel opposed edges. Tube 15 is bonded to one of the edges and positioned relative to slot 19 such that tube 15 minimally obstructs slot 19. Both tube 15 and clip 17 are formed from malleable metallic material which may be manually formed into a resilient desired shape. Clip 17 and the portion of tube 15 that is adjacent to clip 17 are coated with a thin coating 20 comprising an elastomeric material. Device 11 also comprises a short piece of malleable wire 22. One end of wire 22 is affixed to the outer surface of tube 15 near its longitudinal center. The other end of wire 22 extends axially away from clip 17.

As shown in FIG. 3, surgical tool 13 has a pneumatic motor 21, a cylindrical housing or guide member 23, and a rotatable tool implement 25 with a cutting tip extending therefrom. Motor 21, guide member 23 and implement 25 are coaxial with one another. The outer diameter of guide member 23 is slightly larger than the inner diameter of clip 17. A flexible irrigation fluid hose 27 delivers irrigation fluid to tool 11.

In operation, device 11 delivers a stream of irrigation fluid near the cutting tip of rotatable tool implement 25. Depending upon the length of rotatable tool implement 25, device 11 may be oriented or attached to tool 13 in two ways. If rotatable cutting tool implement 25 is of a conventional length (FIG. 3), end 15a will be used to discharge irrigation fluid. If rotatable cutting tool implement 25 is much longer than conventional lengths (not shown), device 11 is inverted and end 15b is used to discharge the fluid.

For a conventional length rotatable cutting tool implement 25, device 11 is attached to tool 13 by inserting guide member 23 into clip 17 so that end 15a is located near implement 25. The user then squeezes clip 17 around guide member 23 to eliminate undesired movement therebetween. The malleable material of clip 17 allows it to clamp around guide member 23. Coating 20 enhances the frictional force between clip 17 and guide member 23. When device 11 is properly installed, clip 17 will be coaxial with guide member 23. Device 11 may be axially repositioned along the length of guide member 23 by forcibly sliding clip 17 in either direction. Wire 22 is wrapped around guide member 23 for additional support of device 11.

The malleable material from which device 11 is constructed allows tube 15 to be repositioned by bending it near end 15a to precisely direct the flow of irrigation fluid relative to implement 25. For implement 25 of greater length, device 11 is inverted and attached in the same manner so that end 15a is attached to fluid hose 27 and end 15b discharges irrigation fluid. After fluid hose 27 is attached to end 15b, irrigation fluid will flow from hose 27, through tube 15 and out of end 15a.

The invention has several advantages. The malleable nature of the device allows the user to bend the tube to more precisely direct the flow of irrigation fluid. In addition, the flexible clip is able to accommodate guide members of various sizes. The design of a single clip located near one end allows the device to be used with short or long tool implements. The clip coating increases the friction between the clip and the guide member while preventing the edges of the clip from scratching or snagging a surgical glove.

While the invention has been shown or described in only some of its forms, it should be apparent to those skilled in the art that it is not so limited, but is susceptible to various changes without departing from the scope of the invention.

We claim:

1. A motorized surgical tool having a longitudinal axis, the motorized surgical tool comprising:
   a housing;
   a rotatable cutting tool implement with a cutting tip extending from the housing;

a motor mounted on the housing;

a cannula having a first end and a second end, each of the ends being adapted to be selectively secured to an irrigation fluid hose so that irrigation fluid flows from the irrigation hose, through the cannula from the one said end connected to the irrigation hose and out the other of the ends for dispensing irrigation fluid near the implement, said cannula being formed of a malleable material such it may be bent to precisely direct irrigation fluid to the rotatable cutting tool implement; and an attachment mechanism rigidly mounted to the cannula closer to the first end than the second end, the attachment mechanism removably mounting the cannula on the housing; and wherein the cannula has a first orientation wherein the first end is located adjacent to the rotatable cutting tool implement and a second orientation wherein the second end is located adjacent to the rotatable cutting tool implement.

2. The motorized surgical tool of claim 1 wherein the cannula is formed from a malleable material such that it may be bent to precisely direct the irrigation fluid relative to the rotatable cutting tool implement.

3. The motorized surgical tool of claim 1 wherein the attachment mechanism is a C-shaped band formed from a malleable material so that it may be secured to housings having a variety of diameters.

4. The motorized surgical tool of claim 3 wherein the band is coated with an elastomer.

5. The motorized surgical tool of claim 1 wherein the attachment mechanism is a generally cylindrical band having a central axis; and wherein the cannula is joined to the band and oriented so that the central axis of the band is parallel to the cannula.

6. The motorized surgical tool of claim 1 wherein the attachment mechanism is a band having a central axis, a C-shaped cross-section with opposed edges defining a longitudinal slot; and wherein the cannula is joined to one of the edges of the band and oriented so that the central axis of the band is parallel to the cannula and coaxial with the housing.

7. The motorized surgical tool of claim 1, further comprising a wire having a first end affixed to the irrigation device and a second end for wrapping around the housing.

8. The motorized surgical tool of claim 1, further comprising an elastomeric coating on the attachment mechanism.

9. The motorized surgical tool of claim 1 wherein the attachment mechanism is a C-shaped band, and wherein the cannula has a diameter which is approximately equal to a thickness of the band.

10. A motorized surgical tool having a longitudinal axis, the motorized surgical tool comprising:

a housing;

a rotatable cutting tool implement with a cutting tip extending from the housing;

a motor mounted on the housing;

a cannula having a first end and a second end, at least one of the ends being adapted to be selectively secured to an irrigation fluid hose so that irrigation fluid flows from the irrigation hose, through the cannula and out the other of the ends for dispensing the irrigation fluid near the rotatable cutting tool implement; and a C-shaped clip having a slot defined by opposing parallel edges, the clip being removably secured to the housing, the cannula being rigidly affixed to one of the edges of the clip and the clip is closer to one of the ends of the cannula than the other of the ends of the cannula; and wherein the cannula is formed from a malleable material such that it may be bent to precisely direct irrigation fluid relative to the rotatable cutting tool implement.

11. The motorized surgical tool of claim 10 wherein the clip is coated with an elastomer.

12. The motorized surgical tool of claim 10 wherein the clip is formed from a malleable material.

13. The motorized surgical tool of claim 10 wherein the cannula has a diameter which is approximately equal to a thickness of the clip.

14. The motorized surgical tool of claim 10, further comprising a wire having a first end affixed to the clip and a second end for engaging the housing.

15. A motorized surgical tool having a longitudinal axis, the motorized surgical tool comprising:

a housing;

a rotatable cutting tool implement with a cutting tip extending from the housing;

a motor mounted on the housing;

a cannula having a first end and a second end, each of the ends being adapted to be selectively secured to an irrigation fluid hose so that irrigation fluid flows from the irrigation hose, through the cannula from the one said end connected to the irrigation hose and out the other of the ends for dispensing irrigation fluid near the rotatable cutting tool implement, said cannula being formed of a malleable material such it may be bent to precisely direct the irrigation fluid to the rotatable cutting tool implement; and an attachment mechanism rigidly mounted to the cannula closer to the first end than the second end, the attachment mechanism being adapted to be removably secured to the housing and thereby removably mount the cannula on the housing.

16. A motorized surgical tool having a longitudinal axis, the motorized surgical tool comprising:

a housing;

a rotatable cutting tool implement with a cutting tip extending from the housing;

a motor mounted on the housing;

a cannula having a first end and a second end, at least one of the ends being adapted to be selectively secured to an irrigation fluid hose so that irrigation fluid flows from the irrigation hose, through the cannula and out the other of the ends for dispensing the irrigation fluid near the rotatable cutting tool implement; and a malleable, C-shaped clip having a slot defined by opposing parallel edges, the clip being removably secured to the housing, the cannula being rigidly affixed to one of the edges of the clip and the clip is closer to one of the ends of the cannula than the other of the ends of the cannula; and wherein the cannula is formed from a malleable material such that it may be bent to precisely direct irrigation fluid relative to the rotatable cutting tool implement.

17. The motorized surgical tool of claim 16, further comprising a wire having a first end affixed to the clip and a second end for engaging the housing.

18. The motorized surgical tool of claim 16 wherein the clip is coated with an elastomer.

19. The motorized surgical tool of claim 16 wherein the cannula has a diameter which is approximately equal to a thickness of the clip.

* * * * *